United States Patent [19]

Klemm

[11] Patent Number: Plant 7,107

[45] Date of Patent: Jan. 16, 1990

[54] GERANIUM NAMED KLEDOL

[76] Inventor: Siegfried Klemm, Hanfacker 8, D-7000 Stuttgart 50, Fed. Rep. of Germany

[21] Appl. No.: 244,999

[22] Filed: Sep. 15, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

The new and distinct geranium cultivar particularly distinguished by its profuse production of very pleasing violet-pink or red-purple flowers, of which each floret has a distinctive white eye, about sixty-five to seventy of these florets forming a nice cluster. Each cluster is carried on a flower stem of about 16 cm in length and extending from a strong stalk about 13 to 14 cm. high, the flowers being displayed above a full body of foliage comprising medium sized leaves having a clearly visible zonation pattern, the foliage body standing about 20 cm. above the soil. The floral persistence is good and the flowers always look clean and tidy with a lasting quality of about fifteen to sixteen days as borne on the plant.

1 Drawing Sheet

BACKGROUND OF THE NEW PLANT

This new geranium cultivar originated as a seedling of a hybrid resulting from my crossing of unnamed varieties selected from my collection of geraniums maintained at my nursery at Stuttgart, West Germany. The varieties selected for producing the hybrid parent of the present plant were developed n the course of inbreeding of the variety 'Rospen' (unpatented) particularly to improve the 'Rospen' variety. The present seedling bloomed for the first time in 1986 and because of its favorable growth and flowering habits, this seedling was successfully propagated by me from cuttings and such propagation was carried on at my direction through successive generations at Stuttgart, which demonstrated that the novel characteristics of the parent seedling would hold true from generation to generation and thus the homogeneity of the new plant can be assured.

DESCRIPTION OF THE DRAWING

This new geranium cultivar is illustrated by the accompanying full color photographic drawing, which shows a potted plant in bloom in illustrating the general characteristics of this variety with respect to both the foliage, the blossoms and the bud clusters, each in various stages of development, the color shown being as true to that herein specified as is reasonably possible to obtain by conventional, professional photographic procedures.

DESCRIPTION OF THE NEW PLANT

The following is a detailed description of my new geranium cultivar based upon observation made in the Fall of 1987 of plants of this variety grown in greenhouse, as well as outdoors, and the color designation is according to The R.H.S. Colour Chart published by The Royal Horticultural Society of London, England.

THE PLANT

Origin: Seedling.

Parentage: Unnamed varieties selected from a group produced by inbreeding the variety 'Rospen' (unpatented).

Classification:

*Botanic.*—*Pelargonium zonale* Hybrid.

*Commercial.*—Potted Geranium.

Form: Quite bushy.

Height: About 34 cm.

Growth: Spreading, compact and upright, with good strength and a medium growth rate.

Branching character: Very good.

Flower stem length: About 16 cm. from a stalk about 13 to 14 cm. high.

Foliage:

*Quantity.*—Moderately abundant.

*Leaf size.*—Medium.

*Shape.*—Orbiculate.

*Margin type.*—Crenate.

*Texture.*—Smooth.

*Ribs and veins.*—Six main veins on each leaf.

*Color.*—Upper side, medium green. under side, lighter green.

THE BUD

Size: Medium.

*Diameter.*—About 11 to 13 mm.

*Length.*—About 14 to 15 mm.

Shape: Generally elliptic.

Rate of opening: Medium.

Color of florets: When sepals first divide, very light frosted pink. When petals begin to unfurl, violet pink.

Sepals:

*Number.*—Five.

*Shape.*—Linear.

*Character.*—The sepals stand up when the flowers open.

*Color.*—Green.

Flower stem:

*Length.*—About 15 to 16 cm.

*Character.*—Erect and rigid.

*Color.*—Green.

THE INFLORESCENCE

Blooming habit: Continuous and profusely from early Spring to late Fall.

Clusters:

*Size.*—Medium.

*Shape.*—In general, round.

*Number of florets.*—About sixty-five to seventy.
*Stalk.*—Length: About 13 to 14 cm. Character: Strong and upright.

Florets:
*Size.*—Medium. Diameter — About 4.5 to 5 cm. Depth — About 1 cm.
*Borne.*—Singly on the umbel stem of a cluster.
*Shape.*—When bloom first opens, cup-shaped. When bloom matures, flat cup.
*Petalage.*—Number of petals: Six or Seven. Arrangement: Imbricated Form: Obovate with entire margin. Texture: Soft Appearance: Satiny Color: Red Purple, R.H.S. 57-D.

Petaloids:
*Number.*—Two or three.
*Size.*—About 7 to 9 mm.
*Color.*—Violet Pink.

Flower stem:
*Length.*—About 16 cm.
*Character.*—Upright and strong.
*Color.*—Green.

Discoloration after first bloom: None.
Effect of weather: None.
Persistence: The flowers always look clean and tidy.
Disease resistance: This plant is resistant to Botrytis as observed in the area of Stuttgart in 1987.
Lasting quality: Good, about fifteen to sixteen days on the plant.

THE REPRODUCTIVE ORGANS

Stamens:
*Number.*—Seven.
*Arrangement.*—Around the ovaries.
*Anthers.*—Size: About 1.6 mm. Color: Orange.
*Filaments.*—Length: About 4.5 mm. Color: White.
*Pollen.*—Color: Orange.

Pistil:
*Number.*—One.
*Style.*—Length: About 4.5 mm. Color: White-pink.
*Stigma.*—Five parts. Color: Nearly White.

Character of ovaries: Normal.

THE FRUIT

Fertility: The fruit is fertile.
Shape: Ovoid.
Color at maturity: Brown.

This new geranium variety is generally recognized by its pleasing clear violet-pink flowers and the bushy, round growth characteristics providing the whole plant with a very attractive appearance.

I claim:

1. The new and distinctive geranium plant substantially as herein shown and described, particularly distinguished by its clear red-purple flowers, of which the individual florets have a distinctive white eye.

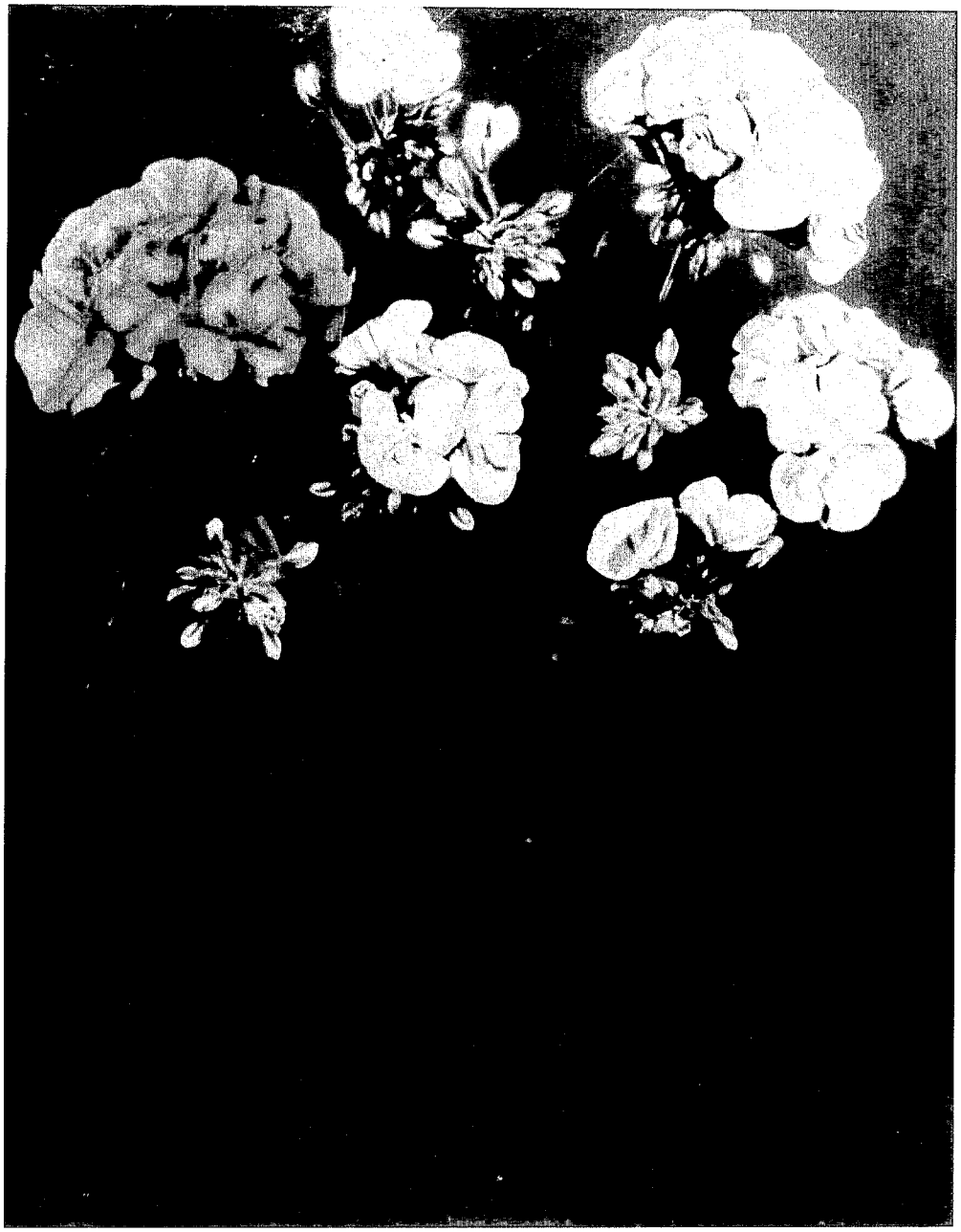

* * * * *